(12) United States Patent
Iqbal et al.

(10) Patent No.: US 7,256,003 B2
(45) Date of Patent: Aug. 14, 2007

(54) METHOD FOR DIFFERENTIATION OF ALZHEIMER'S DISEASE INTO SUBGROUPS

(75) Inventors: Khalid Iqbal, Staten Island, NY (US); Michael Flory, New York, NY (US); Inge Grundke-Ighal, Staten Island, NY (US)

(73) Assignee: The Research Foundation for Mental Hygiene, Inc., Albany, NY (US)

( * ) Notice: Subject to any disclaimer, the term of this patent is extended or adjusted under 35 U.S.C. 154(b) by 441 days.

(21) Appl. No.: 10/890,508

(22) Filed: Jul. 13, 2004

(65) Prior Publication Data
US 2006/0014209 A1    Jan. 19, 2006

(51) Int. Cl.
*G01N 33/53* (2006.01)
(52) U.S. Cl. ...................................... 435/7.1
(58) Field of Classification Search ................ None
See application file for complete search history.

(56) References Cited

U.S. PATENT DOCUMENTS 5,272,055 A    12/1993  Haley
5,445,937 A    8/1995   Haley
5,508,167 A    4/1996   Roses et al.
5,994,084 A    11/1999  Anderson et al.
6,451,547 B1   9/2002   Jackowski et al.
6,495,335 B2   12/2002  Chojkier et al.

OTHER PUBLICATIONS

Hu 2002. American Journal of Pathology 160:1269-1278.*
Iqbal 2002. Tatl tau, A beta (1-42) and ubiquitin in CSF in the diagnosis of Alzheimer disease European Psychiatry 17(1):p. 76S.*

\* cited by examiner

*Primary Examiner*—Robert C. Hayes
*Assistant Examiner*—Daniel E. Kolker
(74) *Attorney, Agent, or Firm*—David L. Nocilly; Bond, Schoeneck & King, PLLC

(57) ABSTRACT

A method for diagnosing distinct subgroups of Alzheimer's Disease, the method comprising the steps of obtaining a sample of cerebrospinal fluid and determining the level of ubiquitin, the level of $A\beta_{1-42}$, and the level of tau present in the sample. Based on the levels of each composition in the cerebrospinal fluid, the sample can be assigned to distinct subgroups.

4 Claims, 1 Drawing Sheet

METHOD FOR DIFFERENTIATION OF ALZHEIMER'S DISEASE INTO SUBGROUPS

STATEMENT REGARDING FEDERALLY SPONSORED RESEARCH OR DEVELOPMENT

Work on this invention was supported, in part, by U.S. Government Funds under Grant No. AG 19158 of the National Institutes of Health (NIH). The government may have certain rights to the invention.

BACKGROUND OF THE INVENTION

1. Field of the Invention

The present invention relates to methods of diagnosing and prognosing Alzheimer's Disease.

2. Description of Prior Art

Alzheimer's Disease is a complex disease that affects the brain. Alzheimer's Disease is one of several disorders that cause the gradual loss of brain cells and is one of and possibly the leading cause of dementia. Dementia is an umbrella term for several symptoms related to a decline in thinking skills. Common symptoms include a gradual loss of memory, problems with reasoning or judgment, disorientation, difficulty in learning, loss of language skills and a decline in the ability to perform routine tasks. People with dementia also experience changes in their personalities and experience agitation, anxiety, delusions, and hallucinations.

It is important for a physician to determine the cause of memory loss or other symptoms. Some dementia or dementia-like symptoms can be reversed if they are caused by treatable conditions such as depression, drug interaction, thyroid problems and certain vitamin deficiencies.

Alzheimer's Disease advances at widely different rates. The duration of the illness may often vary from three to twenty years. The areas of the brain that control memory and thinking skills are affected first but as the disease progresses, cells also die in other regions of the brain. Eventually the person with Alzheimer's will need complete care. If the individual has no other serious illness, loss of brain function itself will cause death.

An early diagnosis of Alzheimer's Disease has many advantages including additional time to make choices that maximize quality of life, lessen anxieties about unknown problems, a better chance of benefiting from treatment and more time to plan for the future.

It is recognized that there is no one diagnostic test that can detect if a person has Alzheimer's Disease. The diagnostic process involves several kinds of tests and may take more than one day. Evaluations typically include consultation with a primary care physician and/or neurologist, a mental status evaluation to assess sense of time and place, ability to remember, understanding, communicate and the ability to do simple math problems, a series of evaluations that test memory reasoning, vision motor coordination of language skills, an examination that tests sensation, balance and other functions of the nervous system, a brain scan to detect other causes of dementia such as a stroke, laboratory tests such blood and urine tests to provide additional information about problems other than Alzheimer's that may be causing dementia and a psychiatric evaluation which provides an assessment of mood and other emotional factors that could cause dementia-like symptoms or may accompany Alzheimer's Disease.

There are a few proposed methods in the prior art for the diagnosis of Alzheimer's Disease. One such method is disclosed in U.S. Pat. No. 5,508,167 to Roses, et al. Roses, et al. discloses a method of diagnosing or prognosing Alzheimer's Disease involving directly or indirectly detecting the presence or absence of an apolipoprotein E-type 4 isoform or DNA encoding apolipoprotein E-type 4 in the subject. The presence of ApE4 indicates that the subject is at higher risk of getting afflicted with Alzheimer's Disease. The patent discloses an immunochemical assay for detecting the presence or absence of the apolipoprotein E4 allele in a subject.

Another method for a differential diagnosis of Alzheimer's dementia is disclosed in U.S. Pat. No. 6,451,547 to Jackowski, et al. The method involves directly detecting the presence of a biochemical marker, specifically human glutamine synthetase in bodily fluids such as blood or blood products. The detection is by an immuno assay incorporating antibody specific to human glutamine synthetase.

An additional method for diagnosing Alzheimer's Disease is disclosed in U.S. Pat. No. 6,495,335 to Chojkier, et al. The patent discloses modified beta-amyloid peptide antibodies that specifically bind the modified amyloid peptides, and methods for using the compositions in the diagnosis of Alzheimer's Disease.

An additional method for diagnosis of Alzheimer's Disease is disclosed in U.S. Pat. No. 5,492,812 to Vooheis. The patent discloses the diagnosis of Alzheimer's Disease based on proteolytic fragments the amino and carboxy terminal amino acid residues of tau proteins that are released from neurofibrillary tangles associated with disease which can be detected in bodily fluids outside the brain.

Although methods disclosed in the prior art are somewhat efficacious in diagnosing Alzheimer's Disease, there remains a need for improved methods and differentiation of Alzheimer's Disease. A major hurdle in developing anti-Alzheimer's Disease drugs has been the lack of means to identify the various subgroups of this heterogeneous disorder and of reliable molecular markers of neurodegeneration that can be monitored in living patients. Thus, to date, all anti-Alzheimer's Disease drugs were developed based on improvement in clinical symptoms i.e. activities of daily living and or cognition as determined by a battery of psychometric tests. Whether these first generation of anti-Alzheimer's Disease drugs, commonly referred to as symptomatic drugs, inhibit the disease process is not known. The present invention demonstrates that there are various distinct patterns of neurodegeneration in Alzheimer's Disease, i.e. subgroups of the disease which can be identified by monitoring the cerebrospinal fluid levels of $A\beta_{1-42}$, tau and ubiquitin, and that the efficacy of therapeutic drugs can thus be monitored by the cerebrospinal fluid levels of these molecular markers.

3. Objects and Advantages

It is therefore a principal object and advantage of the present invention to provide a method for the diagnosis of Alzheimer's Disease.

It is another object of the present invention to provide a method for differentiating Alzheimer's Disease into subgroups.

SUMMARY OF THE INVENTION

A method for diagnosing a distinct subgroup of Alzheimer's Disease, the method comprising the steps of (1) obtaining a sample of cerebrospinal fluid; (2) determining whether the level of ubiquitin is equal or greater than 500 ng/ml wherein a level equal to or greater than 500 ng/ml indicates a first subgroup, if not then (3) determining the level of $A\beta_{1-42}$ equal to or greater than 900 pg/ml and if so assigned as a second subgroup, if not then (4) determining the level of tau equal to or greater than 920 pg/ml and if so, assigned to a third subgroup, if not the (5) determining whether the level of tau is equal to or greater than 520 pg/ml and if so, assigned to a fourth subgroup, if not then assigning to a fifth subgroup.

DETAILED DESCRIPTION

Figure 1:
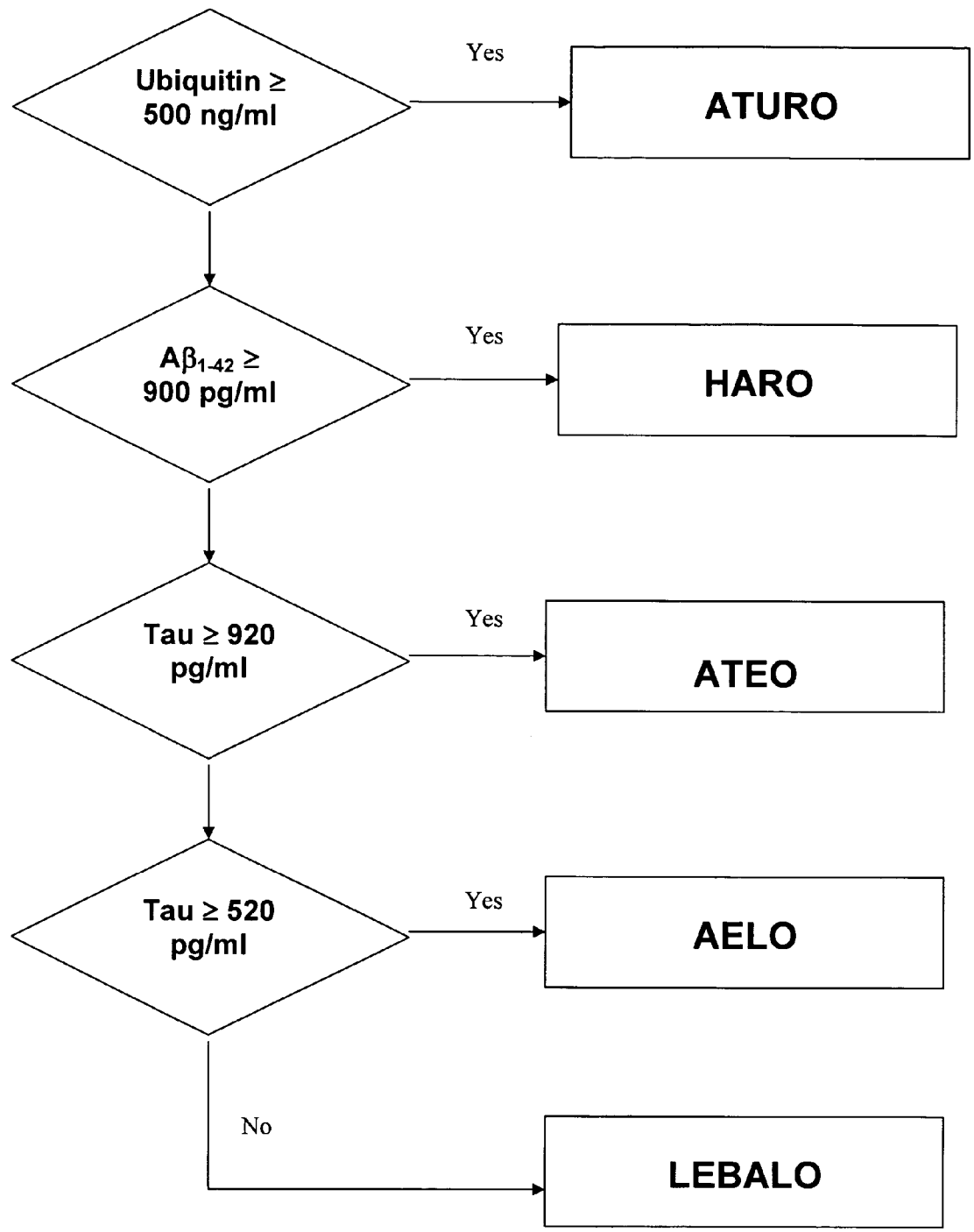
FIG. 1 is a representation of a decision tree for the differential diagnosis of Alzheimer's Disease into subgroups.

Alzheimer's disease (AD), the most common cause of dementia, is multifactorial and both clinically and histopathologically heterogeneous. In less than 5% of cases the disease co-segregates with certain mutations in β-amyloid precursor protein (β-APP), presenilin-1 or presenilin-2 genes. The remaining over 95% of AD cases are not associated with any known mutations and the nature of the etiological agent(s), which could be some metabolic and or environmental factor, is not yet understood. Independent of the etiology, whether genetic or non-genetic, AD is characterized clinically by progressive dementia and histopathologically by the presence of numerous neurofibrillary tangles and neuritic (senile) plaques with neurofibrillary changes in the dystrophic neurites. Because of clinical heterogeneity the diagnosis of AD remains probable till postmortem histopathological examination of the brain, and is made using primarily criteria which exclude other causes of dementia.

The histopathology of AD, i.e. neurodegeneration associated with the presence of numerous neurofibrillary tangles and neuritic (senile) plaques required for a definite diagnosis, shows a considerable qualitative and as well as quantitative heterogeneity. AD can be neocortical type, limbic type and plaque-dominant type and may present with numerous neurofibrillary tangles exclusively confined to the hippocampus and entorhinal cortex. The histopathological heterogeneity of AD is also reflected in the cerebrospinal fluid ("CSF") levels of the proteins associated with these lesions, i.e. Aβ peptide as the major component of Aβ-amyloid from plaques, and tau/phosphotau and ubiquitin from neurofibrillary tangles. A number of studies have consistently shown an increase in the CSF levels of tau/phosphotau and ubiquitin and decrease in $A\beta_{1-42}$ in AD as a group, but there is a considerable overlap between diseased and control cases. We have discovered that AD divides into various subgroups based on the levels of Aβ, tau and conjugated ubiquitin in cerebrospinal fluid.

Levels of tau, conjugated ubiquitin and $A\beta_{1-42}$ were assayed in retrospectively collected lumbar CSFs of 468 patients clinically diagnosed as AD of Lewy body type (AD/L) or AD (353 CSFs), and as non-AD neurological or non-neurological cases (115 CSFs). AD cases fulfilled the NINCDS-ADRDA criteria of probable AD (4) and AD/L diagnosis was based on McKeith criteria. All samples were received frozen in dry ice from two centers (Kuopio University, Finland and University of Goteberg, Sweden) and were kept at 75° C. till used (Table 1).

TABLE 1

Sample Characteristics.

| | | Finland (N = 280) | Sweden (N-188) | Total (N = 468) |
|---|---|---|---|---|
| Age | Mean (SD) | 69.6(9.0) | 73.7(8.5) | 71.2(9.0) |
| Age at dementia onset | Mean (SD) | 70.3(7.1) | 72.9(7.5) | 71.4(7.3) |
| Duration of dementia | Mean (SD) | 2.7(2.6) | 3.3(2.5) | 2.9(2.6) |
| Sex | Female | 62.1% | 63.8% | 62.8% |
| | Male | 37.9% | 36.2% | 37.2% |
| Diagnosis | AD | 68.9% | 75.0% | 71.4% |
| | AD/L | 2.1% | 6.9% | 4.1% |
| | Control | 28.9% | 18.1% | 24.6% |
| ApoE genotype | 3 + 2 | 2.9% | 5.3% | 3.8% |
| | 3 + 3 | 25.4% | 34.0% | 28.8% |
| | 4 + 2 | 1.1% | 2.7% | 1.7% |
| | 4 + 3 | 35.7% | 48.4% | 40.8% |
| | 4 + 4 | 15.7% | 8.5% | 12.8% |
| | Unknown | 19.3% | 1.1% | 12.0% |
| $A\beta_{1-42}$ pg/ml | Mean (SD) | 659.4(246.7) | 615.7(262.9) | 641.9(254.0) |
| Tau, pg/ml | Mean (SD) | 689.6(270.9) | 608.2(289.0) | 656.9(260.9) |
| Ubiquitin, ng/ml | Mean (SD) | 144.2(83.8) | 134.3(85.0) | 140.2(84.4) |

Levels of tau and Aβ-$_{1-42}$ were assayed by sandwich ELISA employing Innotest h Tau Ag and Innotest β-Amyloid$_{(1-42)}$ kits, respectively from Innogenetics (Ghent, Belgium). Conjugated ubiquitin levels were assayed by a competitive inhibition ELISA using as primary antibody, the monoclonal antibody 5-25 (Signet Labs, Inc. Dedham, Mass.) which recognizes the amino acid residues 64-76 of ubiquitin, preferably the conjugated site generated by glycine 76 of ubiquitin with the substrate protein.

Consistent with previous reports, CSF levels of tau and ubiquitin were higher and of Aβ$_{1-42}$ were lower in AD than the control group (data not shown). Patients appeared to cluster into groups according to the combination and extent of abnormalities in the CSF levels of the three marker proteins. The values of the three CSF markers for each subject were taken as indicators, or observable measures, presumed to be determined by AD subtype. Models were estimated in which the number of clusters (subtypes) was fixed at values from 2 to 8. Age was entered as a covariate in all models.

The 3- and 6-cluster models provided the best fit to the data. (Table 2).

TABLE 2

Fit of models by number of latent clusters (subtypes)

| Number of clusters | LL[1] | Number of parameters | BIC[2] (from LL) | Change in BIC | P< |
|---|---|---|---|---|---|
| 2 | −1804.6 | 17.0 | 3713.8 | — | — |
| 3 | −1724.3 | 22.0 | 3583.9 | −129.9 | 0.0001 |
| 4 | −1755.6 | 27.0 | 3677.3 | 93.4 | 0.0001 |
| 5 | −1736.0 | 32.0 | 3668.7 | −8.6 | 0.1261 |
| 6 | −1654.9 | 37.0 | 3537.3 | −131.4 | 0.0001 |
| 7 | −1650.4 | 42.0 | 3559.0 | 21.7 | 0.0006 |
| 8 | −1722.0 | 47.0 | 3733.0 | 174 | 0.0001 |

[1]LL, Log Likelihood;
[2]BIC, Bayesian Information Criterion

The three-cluster model essentially divided subjects into cases and controls, with a third small cluster of apparent outliers. The 6-cluster model, however, fitted the data better with or without consideration of parsimony and yielded clusters that differed substantively within the cases.

Each indicator's level differed for each subtype in its effect on the probability of belonging to that subtype (Table 3a) whereas age had no significant effect on the level of each indicator (Table 3b). Analyses demonstrated that the observed clustering was extremely unlikely to occur in the absence of underlying differences within the sample, and indicated a strong likelihood of multiple categories of subjects differing in some way. The categories represented different subtypes of AD by strong associations seen between these categories and other observed characteristics related to AD and its symptomatic manifestations.

TABLE 3a

Intercept, effects of age and of indicators on cluster membership probabilities

|  | Cluster 1 | Cluster 2 | Cluster 3 | Cluster 4 | Cluster 5 | Cluster 6 | Wald | p< |
|---|---|---|---|---|---|---|---|---|
| Intercept | −3.86 | 13.09 | 1.76 | −6.15 | 2.93 | −7.98 | 56.9 | 0.001 |
| Aβ$_{1-42}$ | −0.5957 | 0.9351 | −0.7065 | −0.6043 | 1.9255 | −0.9543 | 288.6 | 0.001 |
| Tau | 0.0592 | −1.08 | 1.32 | −1.05 | −0.32 | 1.07 | 772.9 | 0.001 |
| Ubiquitin | −0.9654 | −1.23 | −0.63 | −1.56 | −0.81 | 5.20 | 325.9 | 0.001 |
| Age | 0.07 | −0.18 | −0.01 | 0.09 | −0.04 | 0.08 | 57.9 | 0.001 |

TABLE 3b

Intercept for indicators in cluster-membership prediction model

| | Intercept | | |
|---|---|---|---|
| | Coefficient | Wald | p< |
| Aβ$_{1-42}$ | −0.487 | 2.090 | 0.150 |
| Tau | −0.887 | 3.340 | 0.068 |
| Ubiquitin | −0.270 | 0.411 | 0.520 |

TABLE 3c

Direct effect of age on indicators

| | Effect of age | | |
|---|---|---|---|
| | Coefficient | Wald | p< |
| Aβ$_{1-42}$ | 0.008 | 3.205 | 0.073 |
| Tau | 0.015 | 4.937 | 0.026 |
| Ubiquitin | 0.018 | 9.507 | 0.002 |

Standardized mean levels of each of the indicators for each subtype and values of demographic and of potentially validating variable in each of the six classes revealed that the cluster characteristics corresponded in several respects to diagnosis and ApoE genotype (Table 4).

TABLE 4

Characteristics of clusters

|  | Cluster 1 | Cluster 2 | Cluster 3 | Cluster 4 | Cluster 5 | Cluster 6 |
| --- | --- | --- | --- | --- | --- | --- |
| Cluster size | 177 | 101 | 79 | 77 | 30 | 4 |
| (% of sample) | (37.8%) | (21.6%) | (16.9%) | (16.5%) | (6.4%) | (0.9% |
| Number of AD-AD/L and | 171 | 16 | 76 | 67 | 19 | 4 |
| (% of all AD-AD/L cases) | (48.4%) | (4.5%) | (21.5%) | (19.0%) | (5.4%) | (1.1%) |
| Indicator levels |  |  |  |  |  |  |
| $A\beta_{1-42}$ | 532.5 | 895.0 | 490.3 | 513.3 | 1191.6 | 433.8 |
| Tau | 737.4 | 373.3 | 1089.1 | 391.6 | 632.5 | 1010.5 |
| Ubiquitin | 150.2 | 106.4 | 172.7 | 94.0 | 158.0 | 670.0 |
| Age | 75.4 | 60.5 | 70.6 | 76.4 | 70.7 | 75.7 |
| Female | 50% | 45% | 64% | 47% | 56% | 75% |
| Male | 50% | 55% | 36% | 53% | 44% | 25% |
| ApoE genotype |  |  |  |  |  |  |
| 3 + 2 | 0.6% | 8.9% | 0.0% | 3.9% | 13.3% | 25.0% |
| 3 + 3 | 24.9% | 28.7% | 27.8% | 31.2% | 50.0% | 25.0% |
| 4 + 2 | 0.6% | 0.0% | 5.1% | 3.9% | 0.0% | 0.0% |
| 4 + 3 | 55.9% | 15.8% | 36.7% | 53.2% | 20.0% | 0.0% |
| 4 + 4 | 17.5% | 0.0% | 30.4% | 5.2% | 0.0 | 25.0% |
| Unknown | 0.6% | 46.5% | 0.0% | 2.6% | 16.7% | 25.0% |
| Diagnosis |  |  |  |  |  |  |
| AD | 94.9% | 12.9% | 96.2% | 71.4% | 63.3% | 75.0% |
| AD/L | 1.7% | 3.0% | 0.0% | 15.6% | 0.0% | 25.0% |
| Control | 3.4% | 84.2% | 3.8% | 13.0% | 36.7% | 0.0% |
| Origin |  |  |  |  |  |  |
| Finland | 58.2% | 72.3% | 67.1% | 44.2% | 50.0% | 50.0% |
| Sweden | 41.8% | 27.7% | 32.9% | 55.8% | 50.0% | 50.0% |
| Age of dementia onset | 71.7 | — | 66.6 | 73.6 | 71.3 | 71.5 |
| Duration of dementia | 2.6 | — | 3.3 | 2.9 | 1.6 | 1.5 |
| Cluster name | AELO | (Control) | ATEO | LEBALO | HARO | ATURO |
| Sensitivity/Specificity Of assignment using Decision___(percent) | 89/91 |  | 91/95 | 88/98 | 100/96 | 100/100 |

Cluster 1 (AELO), AD with low $A\beta_{1-42}$, high incidence of $APOE_4$ and late onset, the largest cluster (48% of clinically diagnosed AD-AD/L cases), was characterized by low levels of $A\beta_{1-42}$ coupled with relatively unaffected tau and ubiquitin levels (FIG. 1). It comprised 177 subjects, 97% of whom were AD-AD/L patients with a relatively late onset (71.7) of dementia. Seventy-four percent of Cluster 1 cases had one or two $ApoE_4$ alleles ($\chi^{2(1df)}$=17.612,p<0.001).

The 101 subjects in Cluster 2 (74% of the control cases) had levels of $A\beta_{1-42}$ above those of the sample as a whole, and lower levels of tau (FIG. 1). These numbers accorded well with the fact that 84% of subjects in this cluster were non-AD controls. The mean age (60.5) was −15 years younger than members of the Cluster 1. Their ApoE allele distribution corresponded more closely to that of the general population.

Cluster 3 (ATEO), AD with low $A\beta_{1-42}$ high tau, and early onset, which, like the first cluster, was overwhelmingly made up of AD cases (96%), likewise had low $A\beta_{1-42}$ levels but also manifested (unlike the first cluster) considerably elevated levels of tau—approximately 1.5 standard deviations above the mean. Ubiquitin levels were not greatly different from those of the sample as a whole. This cluster (22% of the clinically diagnosed AD cases) was not significantly more likely to possess a type-4 ApoE allele than was the rest of the sample ($\chi^{2(1df)}$=3.612,p=0.07). Among those for whom information was available, age at onset of dementia was relatively early.

The fourth cluster (LEBALO), AD with high incidence of Lewy bodies, low $A\beta_{1-42}$ and late onset, while still predominantly composed of AD cases, included proportionately about five times as many cases of AD with Lewy bodies than did the preceding clusters (15.6% vs. under 3% in all other clusters). levels of all markers were low, and particularly that of tau (FIG. 1). This was the oldest age (76.4) cluster, with the latest onset (age 73.6) of dementia.

The fifth and sixth clusters were considerably smaller (5% and 1% of the clinically diagnosed AD-AD/L cases, respectively), than the first four. Cluster 5 (HARO), AD with high $A\beta_{1-42}$ and recent onset, comprised cases with particularly elevated levels of $A\beta_{1-42}$ (FIG. 1) and relatively recent onset. While its size was insufficient to make meaningful inferences about genotypic and other characteristics, these cases did not appear to have an unusually high probability of possessing an $ApoE_4$ allele.

Cluster 6 (ATURO), AD with low $A\beta_{1-42}$ high tau, high ubiquitin and recent onset, comprised of only four cases, was unusual in that it was the only one showing, along with low levels of $A\beta_{1-42}$ and high levels of tau, substantially heightened ubiquitin levels that were, on average, over 6 standard deviations above the mean.

If we were to take membership in any cluster except Cluster 2 (controls) as an indicator of AD, its sensitivity (or ability to detect a true positive case) would be 95%. Its specificity (or ability to correctly identify a true negative), however, was somewhat lower, but 74% of true negatives would be identified as such. The remaining 26% of true negatives fell into some other cluster. Some of these clinically normal individuals might represent preclinical cases. Interestingly most of these cases fell in cluster 5/subgroup HARO (36.7%) and cluster 4/subgroup LEBALO (33.3%). These two clusters i.e. 4 (LEBALO) and 5 (HARO), which represented less than 25% of all cases examined, had unusual CSF marker level profiles. Cluster 5 (HARO) cases had the highest levels of $A\beta_{1-42}$ and high levels of tau. Cluster 4 (LEBALO) cases had decreased levels of all three markers in the CSF and represented most of the cases of AD with Lewy bodies. The CSF marker profiles of cluster 4 suggest that the Lewy body pathology might play a significant role in the clinical development of the disease in these patients.

To classify diagnosed AD cases into the proposed subgroups we sought a simple set of rules using the level of only one indicator protein at any stage in the classification process. ideally it would classify cases with a sensitivity and a specificity of no less than 90% for each category and a comparable overall level of correct classification. The algorithm must unambiguously categorize all cases. FIG. 1 presents a decision tree based on an algorithm, based on examination of cluster characteristics and experimental runs, that come closest to fulfilling these criteria. The respective sensitivities and specificities with which it classified subjects into the clusters assigned by the latent profile analysis were: AELO: 89%; 91%; ATEO: 91%, 95%; LEBALO: 88%, 98%; HARO: 100%, 96%; ATURO: 100%, 100%. Overall, 86% of cases were correctly classified.

What is claimed is:

1. A method for diagnosing a distinct subgroup of Alzheimer's Disease, the method comprising the steps:
   (1) obtaining a sample of cerebrospinal fluid;
   (2) determining whether the level of ubiquitin is equal to or greater than 500 ng/ml wherein a level equal to or greater than 500 ng/ml assigns said sample to a first subgroup, if not then;
   (3) determining whether the level of Aβ 1-42 is equal to or greater than 900 pg/ml and if so assigning to a second subgroup, if not then;
   (4) determining whether the level of tau is equal to or greater than 920 pg/ml and if so, assigning said sample to a third subgroup, if not then;
   (5) determining whether the level of tau is equal to or greater than 520 pg/ml and if so, assigning said sample to a fourth subgroup, if not then assigning said sample to a fifth subgroup.

2. The method of claim 1, wherein the step of determining the level of ubiquitin includes assaying by competitive ELISA using a monoclonal antibody which recognizes the amino acid residues 64-76 of ubiquitin.

3. The method of claim 1, wherein the level of tau is determined by sandwich ELISA.

4. The method of claim 1 wherein the levels of Aβ 1-42 are determined by sandwich ELISA.

* * * * *

UNITED STATES PATENT AND TRADEMARK OFFICE
CERTIFICATE OF CORRECTION

PATENT NO.       : 7,256,003 B2
APPLICATION NO.  : 10/890508
DATED            : August 14, 2007
INVENTOR(S)      : Khalid Iqbal et al.

It is certified that error appears in the above-identified patent and that said Letters Patent is hereby corrected as shown below:

In The Inventors Names:

Please delete "Ighal", and substitute therefor --Iqbal--.

Signed and Sealed this

Twentieth Day of November, 2007

JON W. DUDAS
*Director of the United States Patent and Trademark Office*